(12) United States Patent
Cabrera (10) Patent No.: US 9,038,638 B1
(45) Date of Patent: May 26, 2015

(54) INFANT PROTECTION ASSEMBLY

(76) Inventor: Jeanette Cabrera, Carolina, PR (US)

( * ) Notice: Subject to any disclaimer, the term of this patent is extended or adjusted under 35 U.S.C. 154(b) by 252 days.

(21) Appl. No.: 13/280,986

(22) Filed: Oct. 25, 2011

Related U.S. Application Data (60) Provisional application No. 61/406,685, filed on Oct. 26, 2010.

(51) Int. Cl.
| | | |
|---|---|---|
| *A61B 19/00* | (2006.01) | |
| *B68G 5/00* | (2006.01) | |
| *A61F 5/37* | (2006.01) | |
| *A47D 13/08* | (2006.01) | |

(52) U.S. Cl.
CPC .............. *A61F 5/3776* (2013.01); *A47D 13/08* (2013.01)

(58) Field of Classification Search
CPC ..................................... A61F 5/3776
USPC .............. 5/424, 100, 93.1, 97, 655; 128/869, 128/846, 870, 871, 95.1, 99.1, 104.1; 119/751, 484, 482; 135/87, 157
See application file for complete search history.

(56) References Cited

U.S. PATENT DOCUMENTS

| | | | | |
|---|---|---|---|---|
| 1,630,941 A | * | 5/1927 | Hood | 5/97 |
| 1,742,011 A | * | 12/1929 | Rumsey | 5/97 |
| 1,812,900 A | * | 7/1931 | Ritzman et al. | 119/751 |
| 5,452,681 A | * | 9/1995 | Ho | 119/498 |
| 6,119,288 A | * | 9/2000 | Hendrickson | 5/97 |
| 6,123,091 A | * | 9/2000 | Flynn et al. | 135/96 |
| 6,216,291 B1 | * | 4/2001 | Eads et al. | 5/424 |
| 6,581,545 B1 | * | 6/2003 | Foster | 119/482 |
| 6,687,930 B1 | * | 2/2004 | Eads et al. | 5/414 |
| 6,859,958 B2 | * | 3/2005 | LaMantia | 5/97 |
| 7,059,274 B2 | * | 6/2006 | Cheng | 119/455 |
| 7,487,744 B1 | * | 2/2009 | Goldberg et al. | 119/453 |
| 7,584,720 B1 | * | 9/2009 | Jackson | 119/472 |
| 7,997,234 B1 | * | 8/2011 | Hughey | 119/496 |
| 2006/0112897 A1 | * | 6/2006 | Moore | 119/482 |
| 2008/0245313 A1 | * | 10/2008 | Jakubowski et al. | 119/497 |
| 2010/0031895 A1 | * | 2/2010 | Pierpont | 119/499 |
| 2011/0226190 A1 | * | 9/2011 | Lamontagne | 119/482 |

\* cited by examiner

*Primary Examiner* — Alireza Nia
*Assistant Examiner* — Tarla Patel
(74) *Attorney, Agent, or Firm* — Luis Figarella (57) ABSTRACT

An enclosure for protecting an infant from smothering by a parent while feeding features one or more load bearing elements supported above a significant portion of an infant's upper body half, an infant supporting bottom surface, and a removable access panel to provide access to the infants face for feeding.

1 Claim, 7 Drawing Sheets

INFANT PROTECTION ASSEMBLY

CROSS-REFERENCE TO RELATED APPLICATIONS

This application claims priority to U.S. provisional patent application Ser. No. 61/406,685 titled "Infant Lactation Protection Assembly", filed on Oct. 26, 2010, the disclosure of which is incorporated herein by reference in its entirety.

PATENTS CITED

The following documents and references are incorporated by reference in their entirety, Carew et al (U.S. Pat. No. 5,822,817), Sher (U.S. Pat. No. 5,367,730), Morton (U.S. Pat. No. 6,370,715), Tishby (U.S. Pat. Appl. No. 2009/0271928), Koessler (U.S. Pat. No. 6,549,140), Welch et al (U.S. Pat. Appl. No. 2005/011008), Forshpan (U.S. Pat. Appl. No. 2007/0056109), Brewin et al (U.S. Pat. No. 7,810,181), Chen (U.S. Pat. Appl. No. 2009/0222971), Straub (U.S. Pat. Appl. No. 2009/0235461), Ward (U.S. Pat. No. 7,587,772) and Morgillo (U.S. Pat. No. 6,499,165).

FIELD OF THE INVENTION

The present invention relates to devices that would protect an infant while being in close proximity with a larger being (such as when being fed), and more particularly to an enclosure that would protect an infant from being accidentally smothered by a parent, such as while feeding or breastfeeding.

DESCRIPTION OF THE RELATED ART

Our present lifestyles demand more and more time of us. In particular, mothers that would like to breastfeed (sometimes called lactate) their infants are challenged by the need to present their breasts to the baby for feeding while at the same time preventing their body from crushing or suffocating the infant. The above is sadly more common than we would prefer, considering that mothers are forced sometimes to do this in the middle of the night before and after long working days.

A nursing mother must create a suitable environment conducive to breastfeeding, including achieving a comfortable and relaxing position for herself and for the infant or baby. The aforementioned possibility of the lactating mother falling asleep, particularly when we consider that infants typically feed around naptimes or even in the middle of the night, mean that the process of breastfeeding must accommodate the needs and safety requirements of a sleeping infant, as well as those of an exhausted mother or caregiver.

A related care issue is that of moving the sleeping infant. In many cases, once the nursing is accomplished, the parent or caregiver will at times be required to go to great lengths to keep their infant unperturbed. In these situations, the infant may fall asleep in an undesirable location and will need to be moved without disturbing the sleeping child. For example, a nursing mother may need or choose to breastfeed their infant in the mother's bed in the middle of the night. In such a case, the mother may wish to move the infant back to a crib or bedside bassinette without waking the infant up. In another example, the mother may prefer to keep the infant in bed, without the risk of said infant falling.

While there are many products available to address some of these infant care issues, they fail to fully answer all the needs described above. Nursing pillows, while providing a comfortable position for the baby and mother during breastfeeding, do not provide a safe sleeping environment, should either the infant or mother fall asleep after feeding. The mother must then move the infant to a safer sleeping environment, which requires disturbing the sleeping infant by lifting the infant from the pillow and moving the infant to the new location. In addition, there is no protection from crushing by the parent's body were him/her to fall asleep.

Many infant nests, which are similar to bassinets, but with an assortment of added foam supports and positioner's, can provide a safe sleeping environment. However, they do not provide suitable access to a nursing mother who wishes to breastfeed the infant in the infant nest.

Thus, a need exists for a device that provides for both the ease and comfort of breastfeeding, or even bottle feeding by dad, as well as, an infant sleeping environment that not only provides for safe positioning of the infant. In many cases, adding the ability to transport the infant were him/her to fall asleep without disturbing said sleep may be critical.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In one aspect the invention is about an infant protection apparatus comprising three or more side support elements extending from three or more points of a datum plane and two or more load bearing elements spanning the gap across the top of said side support elements to form a supporting surface located above said datum plane. In another aspect, it further comprises a roof wall supported by two or more of said load bearing spans, one or more sidewalls covering all or parts of the plane formed by the three points comprised by the ends of a side support element, a load bearing element, and the corner formed by the point where they are joined; a floor surface connected to at least one of the side support elements. It may also further comprise one or more side openings along one or more of the sidewalls, or one or more top access openings, or folding means at or near one or more of said corners or carrying means.

In another aspect, the invention is about an apparatus comprising two or more arcuate frame elements significantly parallel to each other and one or more solid spans connecting said arcuate frame elements, with at least one of said spans being at or above the height of the infant's torso. It may also comprise additionally a significantly solid roof mesh along most of the span between the arches, with an opening for infant positioning or a floor surface connected to at least one of the side support elements or one or more side openings along one or more of the arches thresholds.

In yet another aspect, the apparatus may comprise three or more slightly arched legs, and a central hub wherein at least one end of each said legs is securely attached. In another aspect, it may further comprise folding means along said hub to allow for the rotation of two or more legs parallel to each other or a floor surface connected to at least one of the legs.

Other features and advantages of the present invention will become apparent upon examining the following detailed description of an embodiment thereof, taken in conjunction with the attached drawings.

The above-described and other features will be appreciated and understood by those skilled in the art from the following detailed description, drawings, and appended claims.

DETAILED DESCRIPTION OF THE PREFERRED EMBODIMENT

To provide an overall understanding of the invention, certain illustrative embodiments and examples will now be described. However, it will be understood by one of ordinary skill in the art that the same or equivalent functions and sequences may be accomplished by different embodiments that are also intended to be encompassed within the spirit and scope of the disclosure. The compositions, apparatuses, systems and/or methods described herein may be adapted and modified as is appropriate for the application being addressed and that those described herein may be employed in other suitable applications, and that such other additions and modifications will not depart from the scope hereof.

Figure 1:
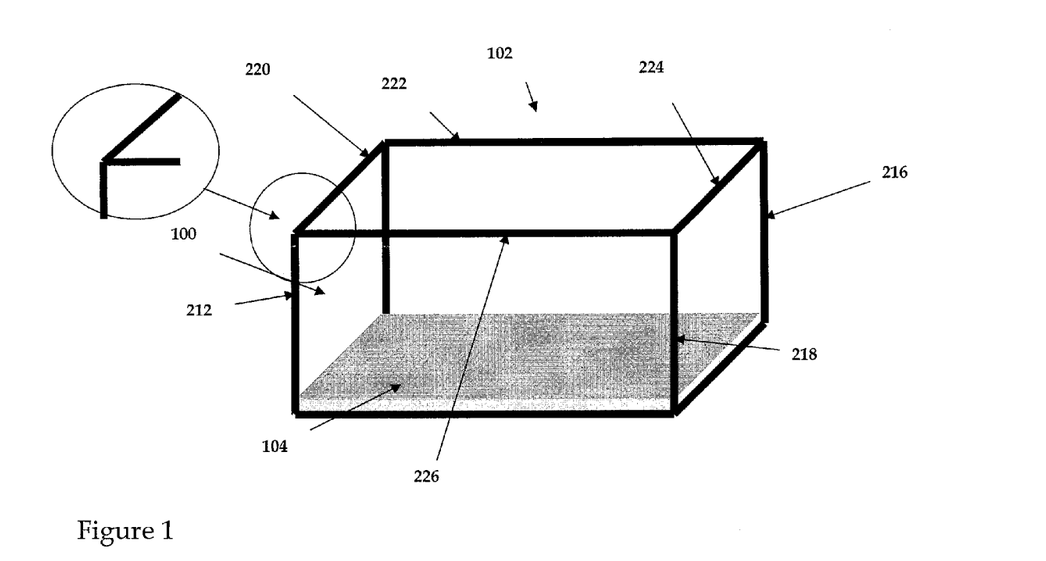
FIG. 1 shows an illustration of the volume that must be optimally protected.
Figure 2:
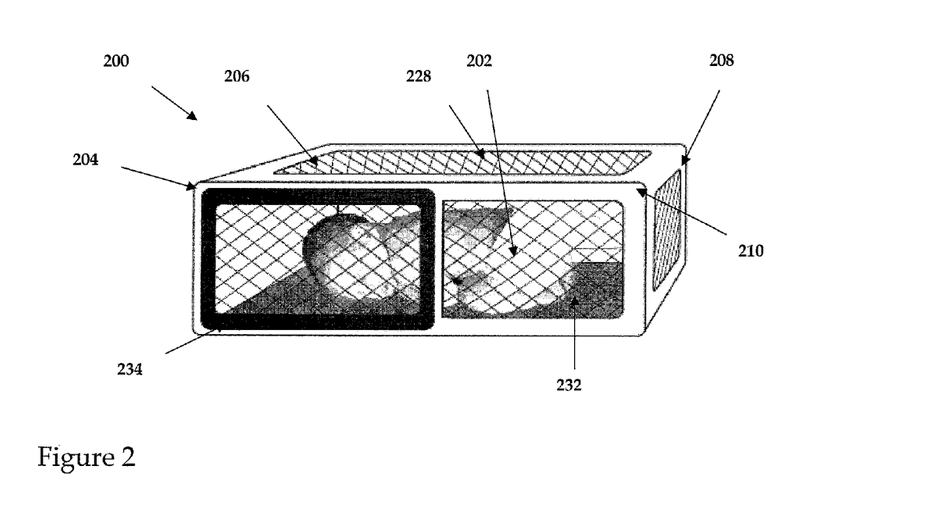
FIGS. 2 and 3 show illustrations of an infant enclosed feeding protection device, according to exemplary embodiments of the invention.

Referring to FIGS. 1-2, we illustrate the invention's basic elements. The primary purpose, is the creation of an infant feeding enclosure that defines a protection envelope 100. Said envelope will have one or more parts of a structural protection structure 102, said structure may include one or more of the structural elements shown. In effect, the protection envelope 100, is formed as shown in the embodiments contained herein. This protection envelope 100 extends above a datum plane, floor or bottom 104 which supports the infant's body. In one embodiment, this is the same as the mattress on which the parent rests, while in another it may be optional bottom surface or floor, which may be connected to one or more of the other structural elements in order to act as a carrier, as well as to deter its displacement in reference to the infant's body. In the case where there is no additional surface or floor The protection envelope or infant feeding enclosure 200 is defined by a six sided volume, enclosing the infant 202. The volumes corners (204, 206, 208, 210) are defined as the point where one or significantly rigid columns or side support elements (212, 216, 218) meet with one or more significantly rigid spanning elements or spans (220, 222, 224, 226) in order to create an anti-crushing or protection frame intended to protect the child's body, especially the head and torso, from being accidentally crushed by the parent's body (or portions thereof, such as an arm), where the parent to fall asleep or become unconscious. This is critical in order to allow the survival of the infant if it were to be crushed by the weight of a sleeping mother.

The corners, columns and spans mentioned above may be constructed from a variety and/or combination of a number of materials. These comprise wood, bone, metals, polymers and plastics (including synthetic or semi-synthetic organic solids, thermoplastic and thermosetting polymers, including polyethylene, polystyrene, polyvinyl chloride and polytetrafluoroethylene (PTFE)). The construction of said corners, columns and spans may include solid, hollow, inflatable and other methods, sufficient to present a structure capable of supporting the parent's body or portion thereof.

In an alternate embodiment, the sides or thresholds of the parallelograms formed by the various possible connections of corners, columns and spans are joined and/or sealed by the addition of rigid, flexible, semi-flexible or such other nets, structures or membranes (228, 230, 232, 234) across its gap or threshold to form a continuous top or roof 228, a bottom 234, as well as sidewalls (230, 232) in any combination thereof. The top element prevents the crushing of the baby by an arm, belly or other portion of the parent's or attendant's body. The side elements, by being placed along all or portions of the thresholds forming the sides, serve to contain the infant within the protected envelope defined by the structural elements (i.e. corner, columns and spans).

These "walls" may be impermeable or permeable, in order to prevent or allow the passage of air and other fluids. In some embodiments, they may have sealable sides (so that when moving an infant it is protected from the elements, but may later be removed to prevent accidental asphyxiation and facilitate temperature control within the volume). A mechanism for comfortably placing or removing the infant is provided through hinges, zippers or VELCRO along the edges of one or more of the walls.

In an alternate embodiment, a floor or bottom surface 234 capable of supporting the weigh of the infant, may be added and connected to the other structural elements. Optional infant securing means may include straps, clips, hooks and loops, VELCRO or other means to ensure the securing of the infant to said floor 234 during transport. Optional carrying means, which may include straps, handles, etc. may be attached to the structural elements to allow the safe transportation of the infant, or the use of the complete unit as a baby carrier or portable bassinet.

To facilitate access to the baby or infant 202 for feeding, breastfeeding or nursing (FIG. 3), one or more lateral access openings 302 and opening covers 304 may be provided. Through these, the parent, guardian or attendant may secure access to the infant's mouth while they are both laying down. The top frame or roof 228 and the spans provide a place for the mother to rest her arms, particularly when presenting a breast to the infant.

Figure 3:
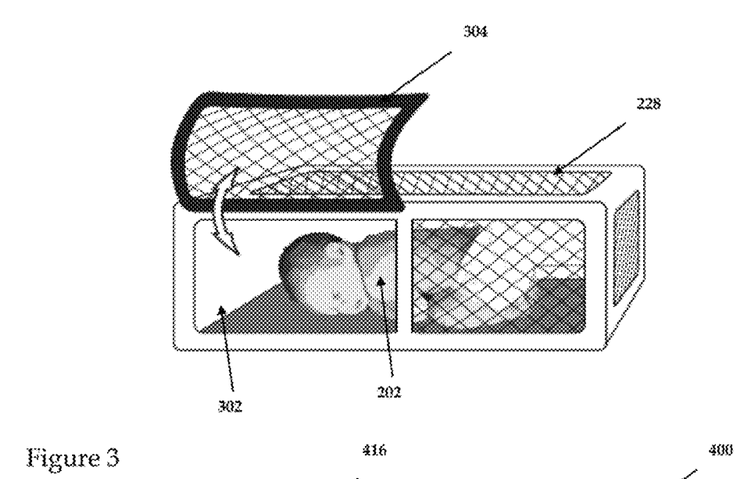

Said openings 302 may be sealed through the positioning of a door, frame, flexible element, moveable or foldable wall, which may be securely positioned in an open or closed position through the use of doors, latches, buttons, hoops and loops, VELCRO and other well known mechanically securing means. In this fashion, when closed, the opening is secured to prevent the unintended or accidental exit of the child. Similarly, the top or cover 228 may have similar opening means, in order to place and remove the child into the unit.

In an alternate embodiment, portions of the corners (204, 206, 208, 210), spans (2220, 222, 224, 226) side support elements (212, 216, 218) are made foldable so that the unit may be flattened for storage when not in use.

In an alternate embodiment 400, two or more arcuate frame elements or arches are used to form the protection envelope or enclosure 100 across all or portions of the infant's body against crushing by the adult's body. In one such embodiment, FIG. 4, two significantly parallel arches 402, 404 are used to define the volume of the protective enclosure 100. In one embodiment, a significantly solid (one capable of preventing compression or folding when under load) roof mesh 412 defines a roof along most of the span between the arches, with an opening 418 through which the infant's body is positioned. The separation between arches, as well as the upper support is preserved by the solidity of the roof 412.

Figure 4:
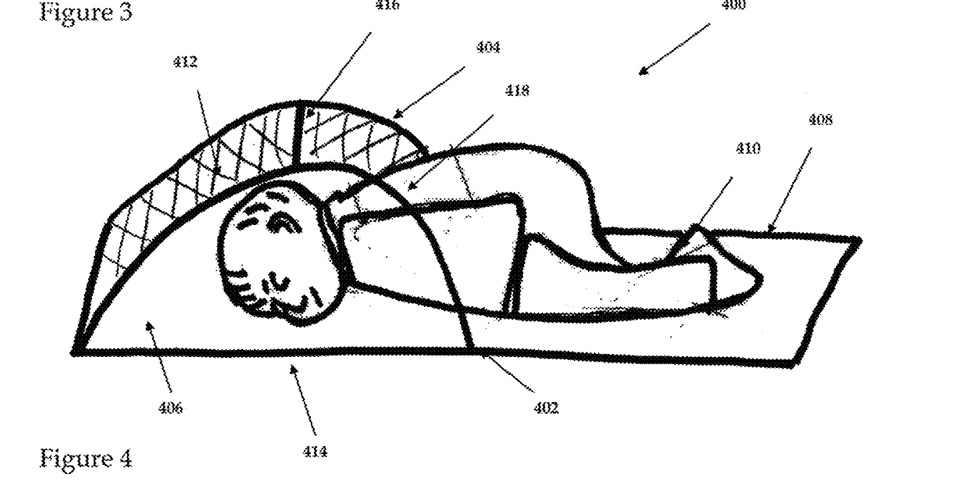
FIG. 4 shows an illustration of a partially enclosed infant feeding protection device, according to an exemplary embodiment of the invention.

An optional carrying surface or floor 406 may be added to facilitate transport of the infant, in combination to either straps or a containment lip 408 with solid or permeable walls 410, 412. Protection against the spans "spreading" under load may be provided by structural cross members or arch supports 414. Said arch supports may join any portion of the arches, including the base or top of these. As before, the lateral access opening, in this case formed by the arch 302 may contain removable opening covers, or not.

In an alternate embodiment, one or more solid spans 416 may be used to prevent the collapsing of the arches towards each other by the weigh of the parent. Alternatively, by making these spans removable and providing a hinge at the base of the arches, the complete assembly may be foldable (placing the arches flat on the floor 406, allowing for easy storage of the unit. Similarly, the floor may be additionally hinged along its length, so that the overall length is halved during storage by folding the floor in half. As before, the unit may have carrying means (handle, etc.) for transport with or without a child in it.

Figure 5A:
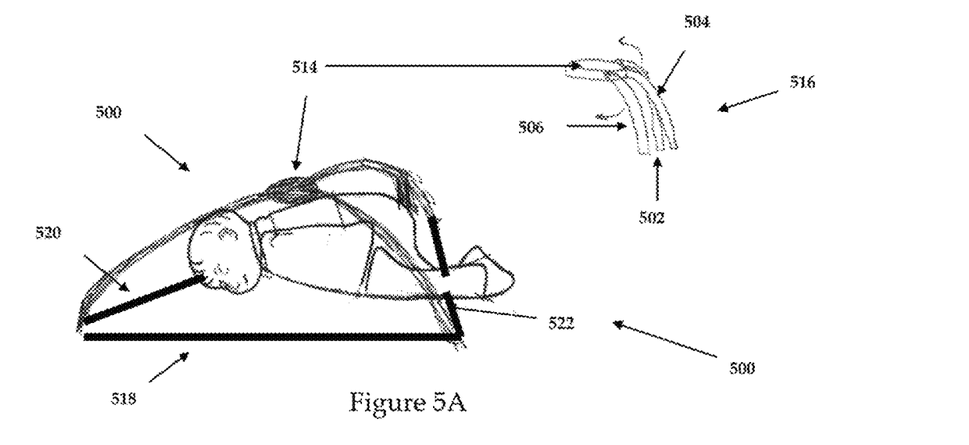
FIGS. 5A and 5B show illustrations of a partially enclosed and foldable infant feeding protection device, according to exemplary embodiments of the invention.
Figure 5B:
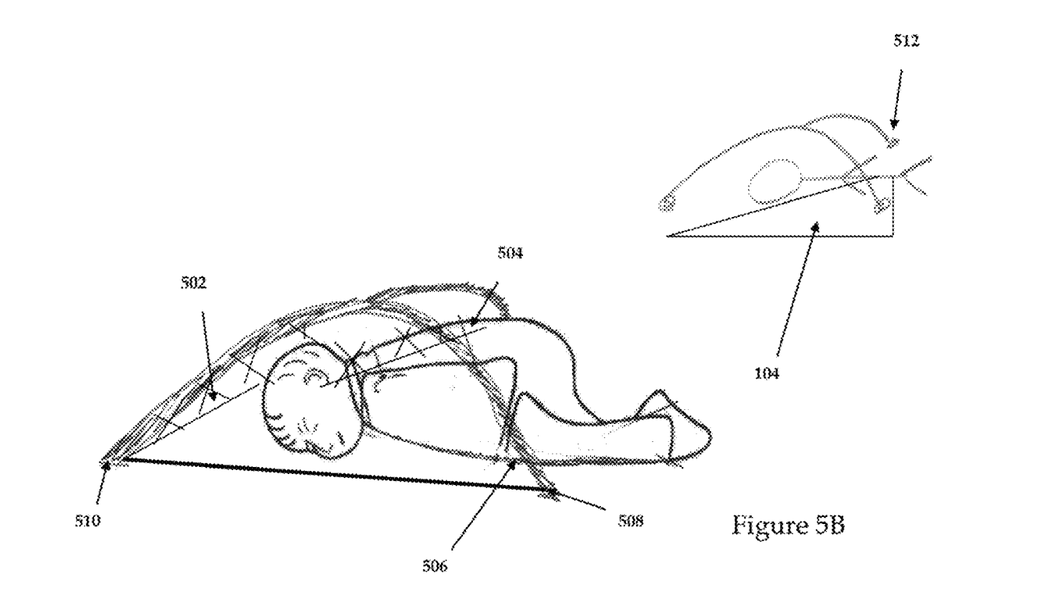

In an alternate embodiment, seen in FIGS. 5A-5B, a partially arcuate structure is employed. Using a triangular base built from portions of arches or other suitable bent structure, the protective feeding enclosure 500 is formed around the infant, allowing a structure that may be placed over the infant by a parent or guardian. While it may be built of straight leg 502, protected volume would be maximized by providing at least a slightly arch or bend to the shape of each leg. Walls or other permeable or impermeable barriers may be placed along the arches, using similar measures as described before to permit the mother access to the infant's mouth or head. To facilitate storage, such a structure could be built with a hub 514 at its apex, so that at least two legs could be rotated parallel to another, facilitating storage of the unit as a folded arch portion 516. To provide further protection against structural failure, a rope, string or strap (518, 520, 522) could be fitted between each of the legs (502, 504, 506) to ensure that the legs are placed by the parent or guardian at the correct position, as well as to provide strength during made to connect the In an alternate embodiment, a floor 104 may be attached to the arches (502, 504, 506) lower portion, in order to provide a platform for liming the displacement of the arches with respect to the infant, or the carrying of the infant. Fixating the arch legs (508, 510, 512) to this floor surface 104 would allow further structural support against failure of the arched structure load.

Of course, the above could be constructed with a minimum of three arches or legs, but alternate embodiments using more may be implemented if so desired. In addition, the arches need not have equal angles between them. Again, as noted before, the structural elements may be solid, tubular, inflatable.

Figure 6:
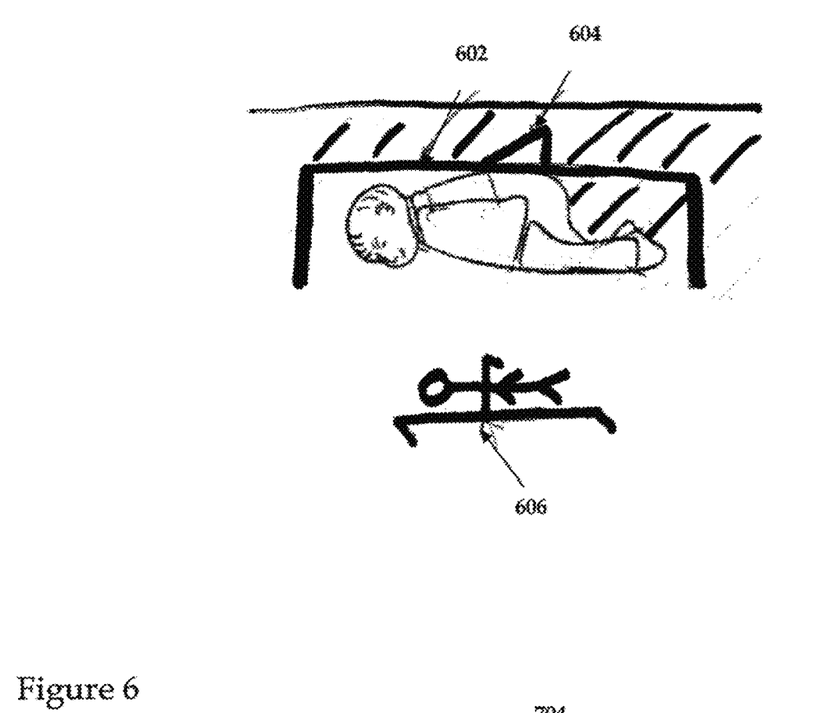
FIGS. 6, 7, 8A, 8B and 9 show illustrations of infant feeding protection devices, according to exemplary embodiments of the invention.

FIG. 6 illustrates a similar tripod application, wherein the supports are rectangular in nature instead of arches. Similarly, the spans 602, 604 need not be limited to a perpendicular joint 606. In the case where an orthogonal angle is used between the spans, the support forms a tripod over the infant. Again, as noted before, the structural elements may be solid, tubular or inflatable. Similarly, a wall material may be laid along part of the threshold, leaving the space in front of the infant's face open.

One measure of protection for the child, would be the utilization of an audible or tactile/vibration alarm placed at the joints. Such an alarm would be capable of detecting either deflation or collapse of the structure, as well as any accidental tipping or displacement. These could be accomplished by an APP for an electronic level equipped smartphone (like the iPhone or iPod from Apple), or a pressure sensor, etc. Upon notification of a failure, the phone could being emanating sounds or vibrations to alert either the nursing parent, or the one resting.

Note that not all solutions need to be separate structural elements. As seen in the exemplary embodiment 700 depicted in FIG. 7, crushing protection structural elements or bumpers 702, 704 could be permanent part of the onesie or infant dress. Similarly, they could be attachable to specially modified dress items via suitably placed latches, buttons, hoops and loops, Velcro and other well known mechanically securing means. By providing a 'guaranteed' volume within its structural members, the infant could be guaranteed of breathing space.

Figure 7:
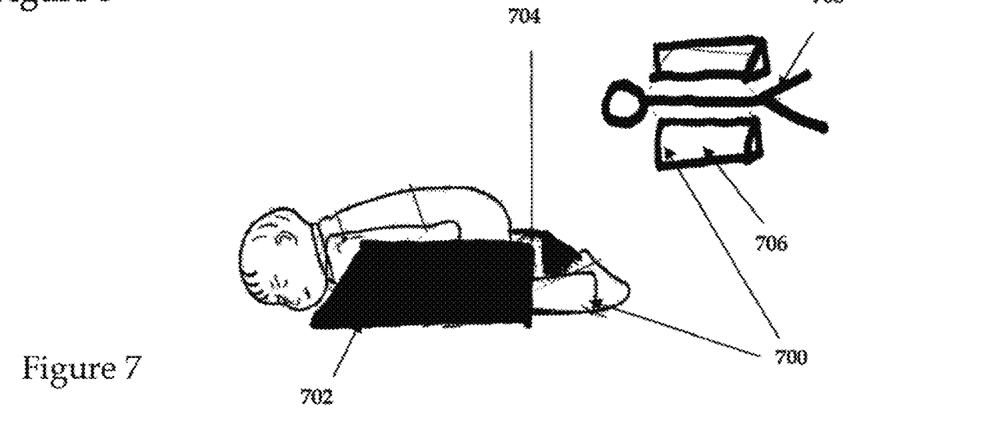

These bumpers 702, 704 could be square, ovoid, circular, triangular or any other shape that would permit the nurse or attendant to place the child's mouth within the appropriate location while at the same time providing it with crush protection. The bumpers may be solid, made of foam, wood, plastic, inflatable or from any other suitable material. In an alternate embodiment, the bumpers are placed on a floor 708 and made into a suitable transporting structure by the addition of infant securing means as described before.

In an alternate embodiment, the outside surface 706 of the bumpers 702, 704 may be shaped so as to discourage pressure against it. For example, bumps, or small protrusions may be formed on its outside surfaces, in order to discourage the parent from pressing against it.

Figure 8A:
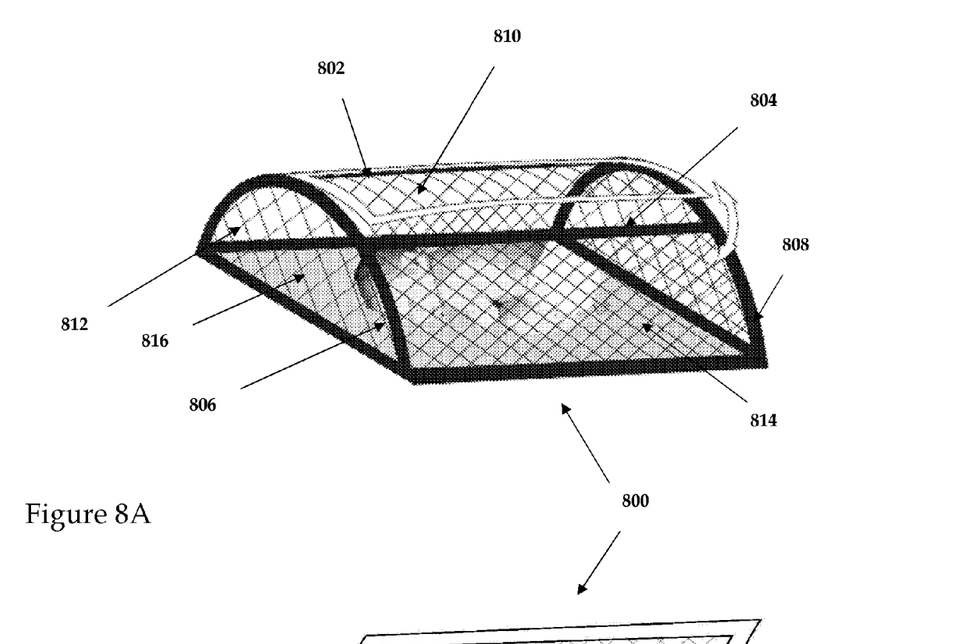
Figure 8B:
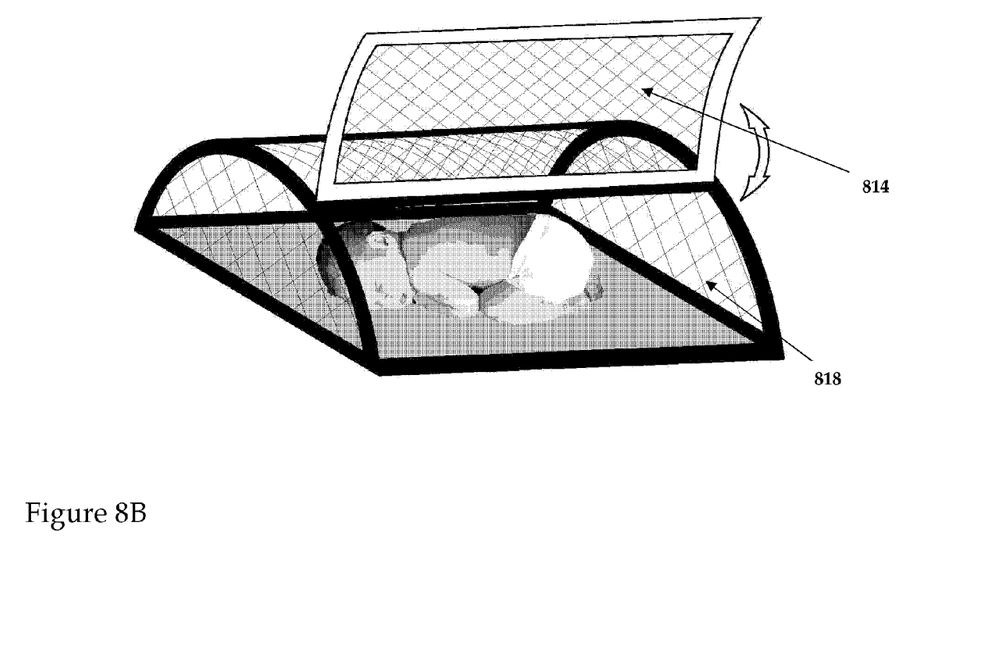

FIGS. 8A-8B illustrate an alternate embodiment where longitudinal elements 802, 804 are combined with arcuate end elements 806, 808 to define the feeding enclosure 100. Note that the longitudinal elements need not be equally spaced, and in fact may be offset to the side the parent is expected to be on. Again, with the addition of walls (810, 812, 814) and a floor 816 from materials as those described above, the unit is capable of functioning as a transportable enclosure. The infant may be placed within the enclosure by the removal of the roof or top wall 810. Feeding may be accomplished by the removal of all or parts of the side wall 814, leaving an opening 818. As before, the unit may be provided with detachable or foldable longitudinal elements in combination with hinges at the base of the arcuate elements 806, 808 in order to facilitate folding and storage of the unit.

Figure 9:
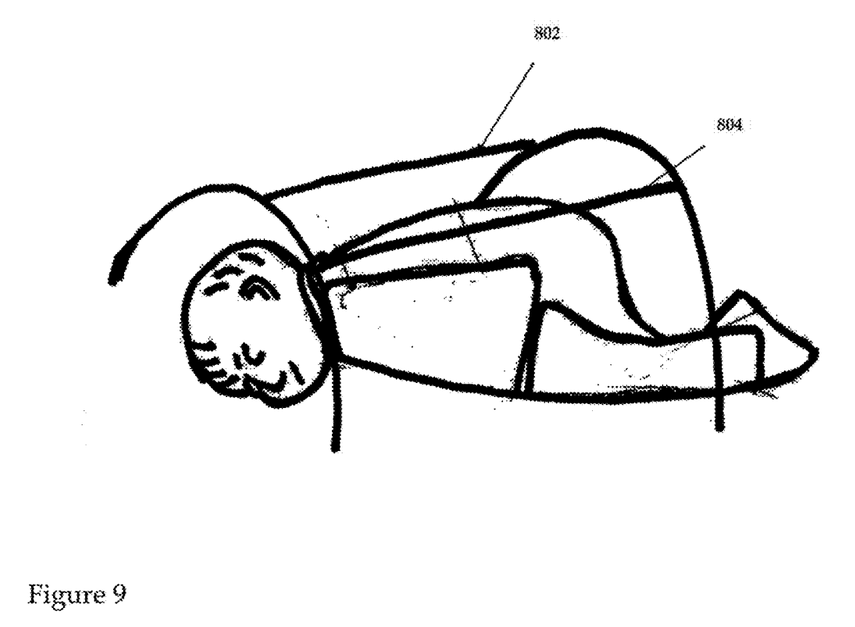

FIG. 9 illustrates an alternate embodiment, wherein the unit is devoid of one or more walls, and it is simply a frame placed over the child sleeping on the parent's mattress.

Figure 10:
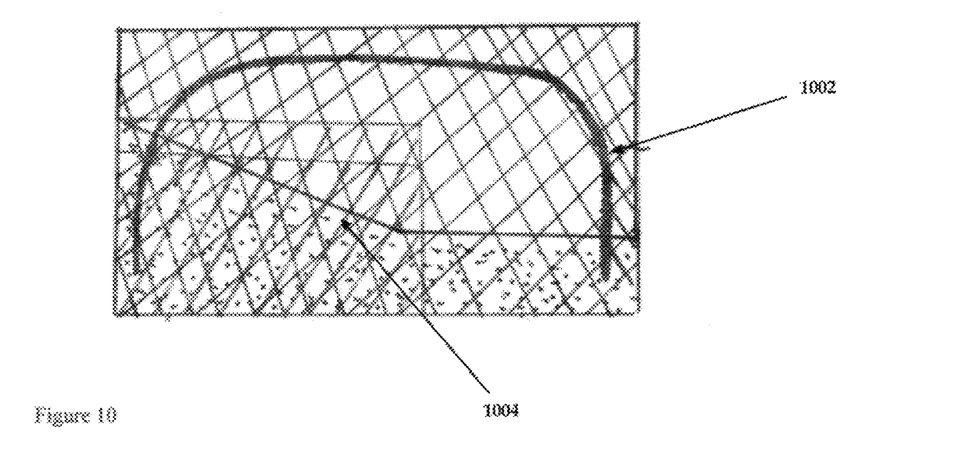
FIGS. 10 and 11 illustrate side views of the infant access portion, according to exemplary embodiments of the invention.
Figure 11:
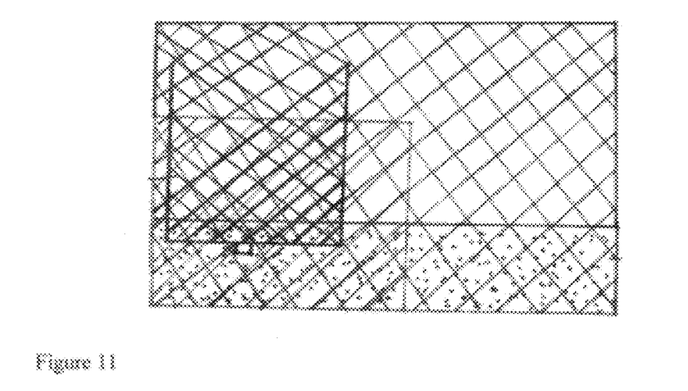

FIGS. 10 and 11 illustrate a cross section of the unit when looking at it from the left side. It must be noted that a mother may decide to nurse from either side (as may a father bottle feeding the child). The side opening 1002 may be implemented either via a VELCRO seam along the edge, a zipper, or any other suitable method. Similarly, the inside may be equipped with a mattress or other suitable padding (made of foam or any other suitable material). This mattress may be inclined 1004 in order to present the baby or infant in a better position for feeding.

CONCLUSION

In concluding the detailed description, it should be noted that it would be obvious to those skilled in the art that many variations and modifications can be made to the preferred embodiment without substantially departing from the principles of the present invention. Also, such variations and modifications are intended to be included herein within the scope of the present invention as set forth in the appended claims. Further, in the claims hereafter, the structures, materials, acts and equivalents of all means or step-plus function elements are intended to include any structure, materials or acts for performing their cited functions.

It should be emphasized that the above-described embodiments of the present invention, particularly any "preferred embodiments" are merely possible examples of the implementations, merely set forth for a clear understanding of the principles of the invention. Any variations and modifications may be made to the above-described embodiments of the invention without departing substantially from the spirit of the principles of the invention. All such modifications and variations are intended to be included herein within the scope of the disclosure and present invention and protected by the following claims.

The present invention has been described in sufficient detail with a certain degree of particularity. The utilities thereof are appreciated by those skilled in the art. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the forgoing description of embodiments.

The invention claimed is:

1. A human infant protection apparatus consisting of:

an integral bottom surface capable of supporting a weight of an infant, said bottom surface having an infant head area located at said bottom's surface near end, and a foot area located at said bottom's surface distal end;

four rigid columns, each column attached and extending from one respective corner of said bottom surface, each said column forming a rigid corner;

four load bearing spans, each said load bearing span anchored to top of two adjacent rigid columns to form a crush resistant side frame, each side frame placed along periphery of said bottom surface and in connection of the four spans to the respective four corners creating a top plane parallel to said bottom surface;

a flexible roof surface spanning one or more of said span elements;

one or more flexible sidewalls each attached to a side frame, each said sidewall covering all or part of the area of said crush resistant side frame;

one or more lateral access openings along a portion of one or more of said flexible sidewalls, each said access opening being at least the size of an infant's head but small enough to prevent the exit of the child, and access opening closure means having mechanical closure means sufficient to secure said closure means in a locked position.

* * * * *